(12) United States Patent
Koczab et al.

(10) Patent No.: US 6,371,951 B1
(45) Date of Patent: Apr. 16, 2002

(54) ABSORBENT PRODUCT HAVING FASTENING MEANS

(75) Inventors: Jean-Pierre Koczab, Tourcoing; Alain Naze, Lille, both of (FR)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/319,707

(22) PCT Filed: Dec. 9, 1997

(86) PCT No.: PCT/SE97/02048

§ 371 Date: Sep. 29, 1999

§ 102(e) Date: Sep. 29, 1999

(87) PCT Pub. No.: WO98/27921

PCT Pub. Date: Jul. 2, 1998

(30) Foreign Application Priority Data

Dec. 23, 1996 (SE) .............................. 9604762

(51) Int. Cl.[7] .............................................. A61F 13/74
(52) U.S. Cl. ..................... 604/385.24; 604/385.27; 604/386; 604/389; 604/390; 604/391
(58) Field of Search ................... 604/385.24, 385.27, 604/386, 389, 391, 390, 385.2

(56) References Cited

U.S. PATENT DOCUMENTS

| | | | | |
|---|---|---|---|---|
| 4,522,853 A | * | 6/1985 | Szonn et al. ................... 428/40 |
| 4,527,990 A | * | 7/1985 | Sigl ............................. 604/385 |
| 5,542,942 A | | 8/1996 | Kline et al. | |
| 5,554,143 A | * | 9/1996 | Roe et al. ................. 604/385.2 |
| 5,772,649 A | * | 6/1998 | Siudzinski .................. 604/386 |
| 5,846,232 A | * | 12/1998 | Serbiak .................... 604/385.2 |
| 6,102,901 A | * | 8/2000 | Lord et al. .................. 604/386 |
| 6,174,303 B1 | * | 1/2001 | Suprise et al. ......... 604/385.29 |
| 6,191,055 B1 | * | 2/2001 | Boyer, III et al. ............ 442/80 |
| 6,193,701 B1 | * | 2/2001 | Van Gompel et al. .. 604/385.01 |
| 6,218,593 B1 | * | 4/2001 | Torimae et al. ............. 604/366 |
| 6,235,011 B1 | * | 5/2001 | O'Connell ................... 604/390 |

FOREIGN PATENT DOCUMENTS

| | | |
|---|---|---|
| EP | 719 532 | 7/1996 |
| WO | 90/07313 | 7/1990 |
| WO | 95/25496 | 9/1995 |
| WO | 96/25133 | 8/1996 |

* cited by examiner

Primary Examiner—John G. Weiss
Assistant Examiner—Michael Bogart
(74) Attorney, Agent, or Firm—Burns, Doane, Swecker & Mathis, L.L.P.

(57) ABSTRACT

An absorbent garment for use in absorbing bodily fluids, having a front waist portion with front attachment means and a rear waist portion with rear attachment means, wherein the front and rear attachment means provide cooperating surfaces allowing attachment of said front and rear attachment means together, wherein the garment has a longitudinal axis extending substantially between mid-portions of the front and rear waist portions, and wherein the front attachment means extends transversely with respect to said longitudinal axis, wherein the front attachment means comprises separate attachment portions and at least one elastic section comprising elastic material, the attachment portions each being attached to said at least one elastic section such that movement of the attachment portions away from each other causes stretching of at least one elastic section.

12 Claims, 3 Drawing Sheets

ABSORBENT PRODUCT HAVING FASTENING MEANS

FIELD OF THE INVENTION

The present invention relates to absorbent garments for absorbing bodily fluids (such as urine, blood or faeces) as defined in the preamble of claim 1. In particular, but not exclusively, the invention relates to absorbent garments of the disposable type. Absorbent garments of the present invention may be of several types, for example diapers (nappies) for adult or infant use, such as incontinence diapers, reclosable absorbent pants (e.g. training pants for infant use), or the like. Typically the garments of this invention will comprise a top sheet, a back sheet and an absorbent body therebetween.

Even more particularly the present invention relates to absorbent garments having cooperating releasable (sometimes known as "reclosable") attachment means.

BACKGROUND OF THE INVENTION

An example of an absorbent garment of the type according to the preamble of claim 1 is known from WO-A-90/07313 for example. The cooperating attachment means disclosed therein are disposed on the front and rear waist parts. On the front waist part, the attachment means comprises two attachment portions consisting of strips of receiving material, which strips are spaced apart so as to lie on either side of an elasticated section of the diaper waistband itself. Such an arrangement means that the elasticated portion of the waistband has to be made to extend from the waist region down to a location between the attachment means. Additionally, attachment of the cooperating hook members to the receiving material is dependent on the elastic arrangement of the waistband itself so that two functions of attachment and waistband extension are dependent on one another which does not allow for optimal fitting of the diaper. Furthermore, the elastic material in the waistband cannot extend laterally beyond the inner margins of the receiving material since otherwise attachment of the receiving material on to a gathered section would result in unsatisfactory results.

A further known prior art arrangement is shown in EP-A-0 491 347. This document discloses a disposable diaper in which the front attachment means on the front waist portion of the article is constituted by a strip of loop material. In one embodiment, said strip is affixed to the impermeable back sheet by means of spaced beads of adhesive, thus allowing tension forces applied thereto (by the attachment of hook tabs) to distort and buckle portions of the loop strip. In this way the peel, shear and latching forces can be altered. In a further embodiment, the hook tab members can be made of elastomeric material.

In a further prior art document WO-A-95/25496, also aimed at altering the peel strength between hook and loop attachment materials, a landing member of loop material having slits therein may be attached around its whole periphery to the front waist portion of an absorbent article. In one embodiment, it is disclosed that the integrity and appearance of the landing member may be better preserved when under tension if an elastomeric adhesive is used to secure the landing member inside the said peripheral attachment line. In this way, when tension forces are released from said landing member, the landing member will return to its undeformed condition.

The aforementioned systems thus relate to achieving a change in the peel strength between the hook and loop members.

Whilst EP-A-0 491 347 provides elastication of the hook tabs to produce the desired effect, this has the disadvantage that the elastication forces are constrained to be at the two side portions of the article. Additionally a wrinkling or lifting of the front attachment means may occur.

The object of the present invention is to provide an absorbent garment having attachment means (not restricted to hook and loop types) which provides a better fit around a wearer of said garment and thus provides a high degree of comfort to the wearer.

SUMMARY OF THE INVENTION

In one embodiment, the an absorbent garment for use in absorbing bodily fluids has a front waist portion with front attachment means and a rear waist portion with rear attachment means, wherein the front and rear attachment means provide cooperating surfaces allowing attachment of said front and rear attachment means together, wherein the garment has a longitudinal axis extending substantially between mid-portions of the front and rear waist portions and wherein the front attachment means extends transversely with respect to said longitudinal axis, wherein the front attachment means comprises two separate attachment portions and at least one elastic section comprising elastic material, the attachment portions each being attached to said at least one elastic section such that movement of the attachment portions away from each other causes stretching of at least one elastic section.

Preferred features of the invention are defined in the dependent claims.

Further features applicable to the invention will be clear from the following description.

The term "mid-portion" of the front and rear waist portions, as used to define the position of the longitudinal axis (X—X) of the garment, is intended to refer to a position approximately mid-way between the longitudinal side edges of the absorbent garment in the region of the front and rear waist portions. Since the exact location of a mid-way portion may vary due to manufacturing tolerances or asymmetry, such term is to be regarded as defining a location in the mid-region of said waist portions.

The term "waist portions" of an absorbent garment refers to the general areas at either end of the absorbent garment which are designed such that, when fitted to a user, they will be proximate to the front and rear portions of the user's waist. The waist portions will often be provided with elastication means. In a diaper, these front and rear waist portions will start at an outer longitudinal edge of the diaper and extend towards the middle of said diaper by a certain distance, typically between 30 mm (typical in very small diapers) up to about 120 mm in adult incontinence diapers. The two waist portions will be joined by an intermediate region, the side edges of which are typically substantially taken up by leg-opening portions which may be elasticated. A typical ratio of proportions in a diaper is such that the extent of the waist portion inwardly towards the middle of the diaper constitutes between about 20% to 40% of the whole diaper length. Expressed in other terms, the extent of the front waist portion, when a correct size diaper is fitted correctly on a wearer, can be seen as approximating to the distance from the upper edge of the diaper, when fitted, to the top of the user's thighs.

The term "front waist portion" is intended to refer to the portion of the garment which will normally be positioned at the front of the wearer when the garment is correctly fitted as intended. However, the garment can be fitted back-tofront, in which case the front waist portion will be positioned at the wearer's lower back.

An "elastic material" is intended to indicate a material which has highly elastic properties. For the purposes of this invention, such elastic properties include materials having a degree of elastic extension compared to their relaxed (non-tensioned) state being typically above 25%, more preferably above 50% and most preferably above 100%. Even more preferably, elastic materials will be used which have a degree of elastic extension compared to their relaxed state in the order of up 200% to 500% or even more in some cases. Such materials include, by way of example only, natural rubber films or polyurethane rubber (P.U.R) films, or thicker elasticated sheet materials having good elastic properties. Such materials are not to be confused with materials such as non-woven materials or the like which have elastic extensions of some 4% or less.

The exact characteristics chosen for the elastic material will be adapted to the particular type and size of absorbent garment. Thus the elastic strength, memory of the elastic film used, weight, suppleness and strength will be varied in accordance with the requirements of any specific type of garment. The term "elastic extension" also means that the material, when stretched, will return to it original length within certain limits. Such limits are more commonly referred to as the memory of the material. Whilst the elastic material ideally has a high memory such that it will return substantially completely to its original length when a tensioning force is released, for the purposes of this invention elastic materials returning to between 100% to about 115% or more of their original length after being stretched by at least 25% are suitable for example.

Additionally it is to be understood that the absorbent garments referred to in claim 1 may include an absorbent body, or member, as an integral part thereof, or that they may be of the type where an absorbent body or absorbent member is added. The latter type may, for example, be of the type where a garment where absorbent body or element is removable, such as in the case where the same absorbent garment is to be used several times with a replaceable absorbent body.

The front and rear attachment means are defined as having cooperating surfaces. By this it is meant that each of said first and second attachment means has a surface which will engage with, preferably in a releasable manner, the respective opposed attachment means. A preferred form of this, having regard to the present invention, would be hook and loop fastening means (known per se). Hook and loop fastening means are merely an example of what are known generally in this technical field as releasably attachable fastening means and more particularly as releasably attachable mechanical fastening means. The hook and loop attachment means thus provide mechanically interengaging, or in other words mechanical cooperation, between each other. An example of such mechanical fastening means is for example sold under the trademark "Velcro". Various types of releasably attachable mechanical fastening means are known in this field and are to be understood as included within the definition of attachment means providing cooperating surfaces. Thus where hook and loop elements or strips are referred to, it should be understood that this is merely an example and that adhesive cooperating means of releasable or non-releasable type may also constitute the front and rear attachment means respectively. Additionally the term "hook element" should not be interpreted narrowly and this term may include elements which are not precisely in the form of a hook, but may also be "mushroom" shaped (as is known per se).

BRIEF DESCRIPTION OF THE DRAWINGS

The invention will now be described in more detail with reference to certain preferred embodiments, one of which is shown in the accompanying drawings, and where.

DETAILED DESCRIPTION OF PREFERRED EMBODIMENTS

Figure 1:
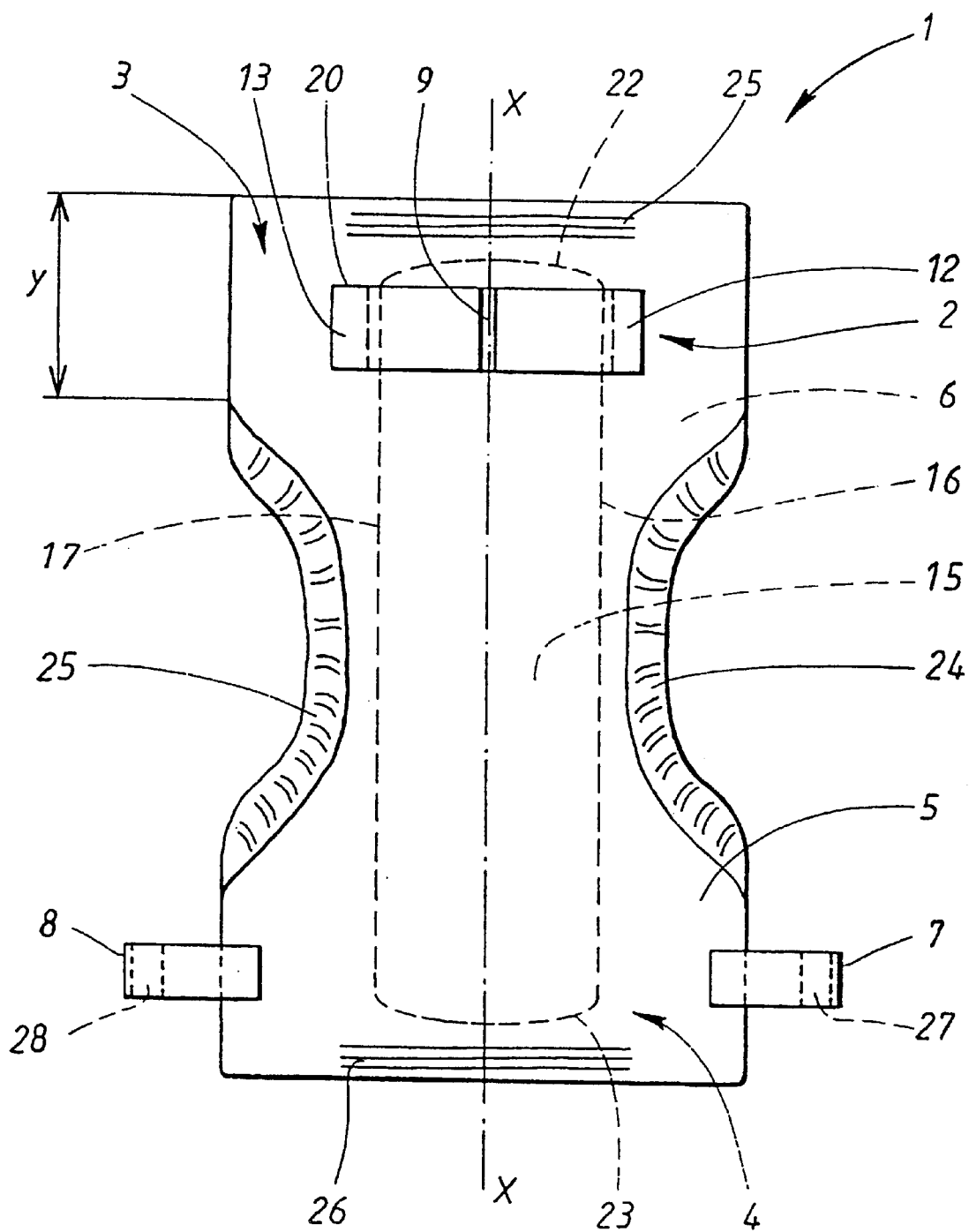
FIG. 1 shows a plan view of an absorbent garment according to the invention, said garment being laid flat with its back sheet visible.

The absorbent garment 1 illustrated in FIG. 1 is shown in a laid-flat condition. The garment has a generally longitudinal axis X—X extending between the mid-way portions of the front waist portion 3 and the rear waist portion 4 respectively. The garment has leg opening portions 24 and 25 which are preferably elasticated, as well as front and rear edge, preferably elasticated waist portions 25 and 26 respectively. The garment includes a back sheet 5 (i.e. the side facing the user's clothes during use) and a top sheet 6 or liner on the opposite side. Between said sheets is an absorbent core 15 shown in dashed lines, having longitudinal side edges 16 and 17 and end edges 22 and 23.

On the front waist portion 3 there is a front attachment means 2, sometimes referred to as a landing zone. Said means 2 will be described in greater detail below. On the rear waist portion there are positioned rear attachment means 7 and 8, preferably in the form of two tab elements as shown. The attachment of said rear attachment means 7 and 8 is known per se in the art and thus needs no further description.

In the embodiment shown, attachment means 7 and 8 each comprises a strip 27, 28 of attachment elements (e.g. hook elements of a hook and loop attachment), said attachment elements being shown in dashed lines, as these are integrated with the tabs on the underside thereof in the view shown. The attachment means 7, 8 are of a type which will cooperate, preferably in a re-releasable manner, with corresponding surfaces on attachment means 2 (e.g. loop means).

The attachment means 2 comprises a substantially elongate strip, suitably of a dimension of 40 mm by 170 mm where the front waist section has a length y of about 120 mm, said strip having two longer transverse edges 20 and 21 (see FIG; 2) and two shorter edges 29 and 30. However, the means 2 may be oval or of other shape and the dimensions may vary somewhat according to the size of garment and the transverse width of the absorbent core.

The attachment means extends from one edge 29 to the opposite edge 30 across the longitudinal axis X—X of the garment and is fixedly secured to the back sheet 5 preferably at locations 12 and 13 (see also FIG. 4) lying outside the absorbent core's edges 16 and 17. However, the attachment locations may also lie within the area bounded by the dashed lines 16, 17, 22, 23, of the absorbent core. For example, where a T-shaped, I-shaped or other non-rectangular absorbent core is used, the attachment zones 12 and 13 can lie within the bounds of said shape, although preferably at locations which are in approximate longitudinal alignment with the inner regions of the leg openings and/or elastication of these areas, or just inwardly thereof. The attachment zones could also be located further outwardly.

Similarly, the means 2 has its upper edge 20 (as depicted) lying at a level within the end edge 22 of the absorbent core. This relative positioning is particularly preferable, since the edge 20 may be fairly stiff in certain constructions and thus can otherwise be felt through the layers 5 and 6 by the wearer. In a preferred embodiment, the distance between the upper edge 20 of the attachment means 2 and the upper edge 22 of the absorbent core may suitably be about 5 mm, said 5 mm being measured at a location coincident with the longitudinal axis X—X.

The attachment means 2 comprises an elastic material section 9, said section preferably being fixed to said back sheet proximate or overlying the longitudinal axis X—X. Said fixing at said central point is preferred since otherwise the strip means 2 may move upwardly or downwardly with movement of the wearer during fitting of the garment and during use. When an attachment of the elastic section 9 at this location is provided, the attachment preferably comprises any suitable elastomeric adhesive (known in the art). This provides a resistance to tearing of the attachment between the means 2 and the back sheet 5 when handling the garment roughly. Moreover, when the back sheet, as is commonplace currently, is made of polyethylene (PE) and the elastic portion is made of rubber, a good adhesion between the two parts is achieved.

Figure 4:
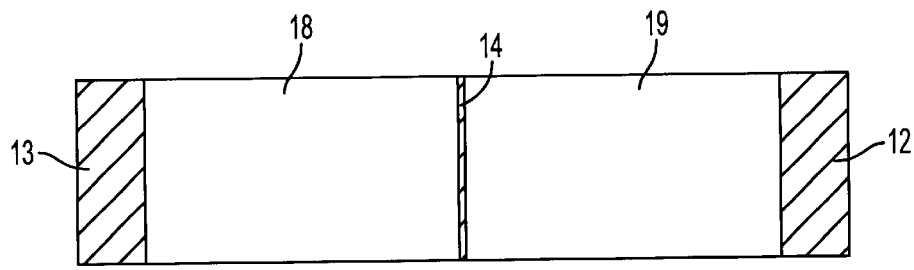
FIG. 4 shows a rear view of the front attachment means depicted in FIG. 2, illustrating where the attachment means is attached to the outer sheet of an absorbent garment.

With reference to FIG. 4, the attachment of the elastic section 9 to the back sheet 5 is preferably over an area 14 having a transverse width of between about 0.5 mm and 2 mm, although a larger attachment width may be used. Clearly, the less adhesive used, the cheaper the product will be and thus use of adhesive should be minimised.

When used, the adhesive should however preferably have an adhesive strength to the underlying material which is greater than the break strength of said material. Thus, exertion of a pulling force on the strip means 2 either parallel to, or perpendicular to, the back sheet 5 should result in tearing of the back sheet and not tearing of the adhesive itself. The adhesive strength of the bond between the overlying strip 2 and the adhesive will normally be lower than the breaking or tear strength of the strip 2.

Figure 2:
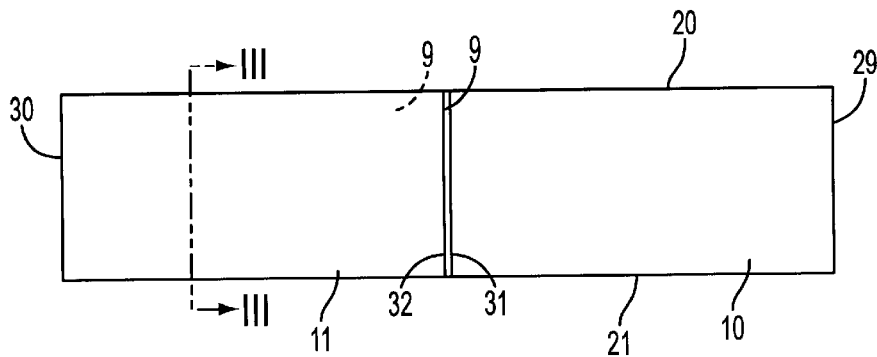
FIG. 2 shows an enlarged view of one embodiment of the front attachment means, as seen in FIG. 1.

As shown in FIG. 2, the attachment means 2, comprises two attachment portions 10 and 11 joined between their inner facing ends 31 and 32 by means of an elastic material section 9. Each of said attachment portions 10 and 11 (for example non-elastic strips of loop elements) is fixedly attached to said elastic section 9, typically with a small gap of about 1 mm or so between said ends 31, 32.

Figure 3:
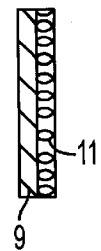
FIG. 3 shows a cross-sectional view through the front attachment means along line III—III of FIG. 2.

FIGS. 2 and 3 shows the attachment means (strip) 2 having a preferred construction. In said construction, the attachment means 2 is made by attaching two strips 10 and 11 to a continuous film of elastomeric material which extends substantially from one edge 30 to the other edge 29 of said means 2. Since the loop material strips are non-elastic, it is however clear that the elastic material section 9 itself will be constituted by the area of elastomeric material lying between the inner edges 31 and 32 of the opposed strips 10 and 11. The attachment of said elastomeric section 9 material to the strip 11 can be seen in cross section in FIG. 3.

For the skilled man it will however be apparent that material could be saved by having a narrow strip of elastomeric material between the inner edges 31 and 32, and only a small attachment portion (for attachment of said strips 10 and 11 to said elastomeric strip) lying transversely outwardly of said inner edges. The outer ends of said strip elements 10 and 11 would then themselves be attached directly to the back sheet by suitable adhesive. Additionally, if desired, more than one elastic section 9 could be included in the attachment means 2, although only one is needed.

FIG. 4 shows the attachment means 2 from the opposite side. In this embodiment, the hatched areas 12, 13, 14 define attachment zones. Zones 12 and 13 may suitably have a width of about 20 mm and a length (which in this case is the same length as that of the attachment means 2) of about 40 mm. Variations of these dimensions may of course occur. The non-hatched areas 18, 19, in FIG. 4 constitute zones or areas of non-attachment. For purposes of clarity it is merely confirmed that no attachment of the means 2 to the backsheet occurs throughout the whole of these non-hatched areas 18 and 19 including the upper and lower edge portions 20, 21 thereof.

The attachment of the various zones 12, 13 and 14 may occur in any known suitable manner. Typically ultra-sonic adhesion or adhesion by means of hot-melt adhesives or the like may be employed for zones 12 and 13. Rubber based adhesives or APAO-based adhesives (amorphous polyalfaolefin) may also be used for example.

The attachment means 2 can be constructed in-line by feeding individual strips (of the type indicated as 10 and 11) on to an elastomeric material which is also being fed. These can then be applied as a combined unit and adhered at locations 12, 13 and 14 to the back sheet. Either transverse or longitudinal garment production techniques are suited to the application of said attachment means 2.

Alternatively, the attachment means 2 may be formed off-line as a series of separate strips, or as a continuous strip which is cut during or just before application to the backsheet. Various other construction and application methods will be clear to the skilled man upon reading this description.

Figure 5:
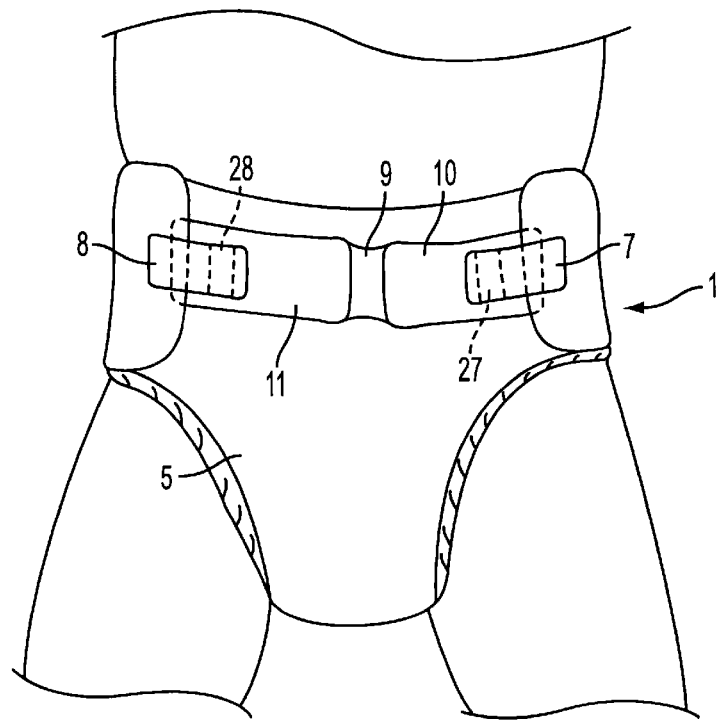
FIG. 5 shows a garment according to the invention in its position of use on a wearer.

One embodiment of a garment 1 of the invention is shown in FIG. 5, fitted to a wearer. As will be clear, also from the figure, the rear attachment means strips 7 and 8 have been attached by means of their attachment surfaces 27 and 28 to the cooperating surfaces of strips 10 and 11. When attaching the strips in this manner a tensile force is applied to the strips 7 and 8 before they are placed onto the strips 10 and 11. To provide a comfortable fit and an equalisation of the tensile force along the front of the waist portion, the elastic section extends (as shown in the figure) from a width of (say) 1 mm to a width of (say) 5 mm. Additionally, even if the elastic portion is only extended partially with regard to its maximum elongation when first attached, movements of the wearer and changes in the body size at this location will be accommodated by stretching of the elastic portion 9 still allowing a comfortable fit.

Additionally, since the attachment means 2 extends over the absorbent core, the tensile forces in the attachment means 7, 8 and 2 (transmitted to the body as compressive forces) will be cushioned by the effect of the core, thus further increasing comfort.

With the use of adhesive in the section 14, an effect will also be created whereby the forces in the whole waist section can be spread differently between the left side and the right side of the waist portion. Such is beneficial if for example the user experiences discomfort on one side of the waist portion, allowing that portion to be fitted more loosely whilst still providing a good fit.

Although the invention has been described with respect to certain particularly preferred embodiments thereof, the invention is not restricted to said embodiments and can instead by varied widely within the scope of the appended claims.

For example, although the strips 10 and 11 are described as having inner edges 31 and 32 separated from one another by a certain distance, the strips may be arranged to be overlapping in the central portion, as long as at least a minimal area of non-attachment is left between the points of attachment of said strips 10 and 11 to said elastic section 9.

Whilst the strips 10 and 11 have been shown as being co-extensive and co-terminous with their respective sides of the elastic film to which they are attached, such is not a requirement and the strips may be smaller or may be larger in area than said underlying elastic film.

Although the elastic film is described as underlying the strips 10 and 11, it may of course overlie said strips, as long as sufficient area is provided for at least partial attachment of said rear attachment means 7, 8 to the cooperating attachment surfaces of said front attachment means.

Figure 6:
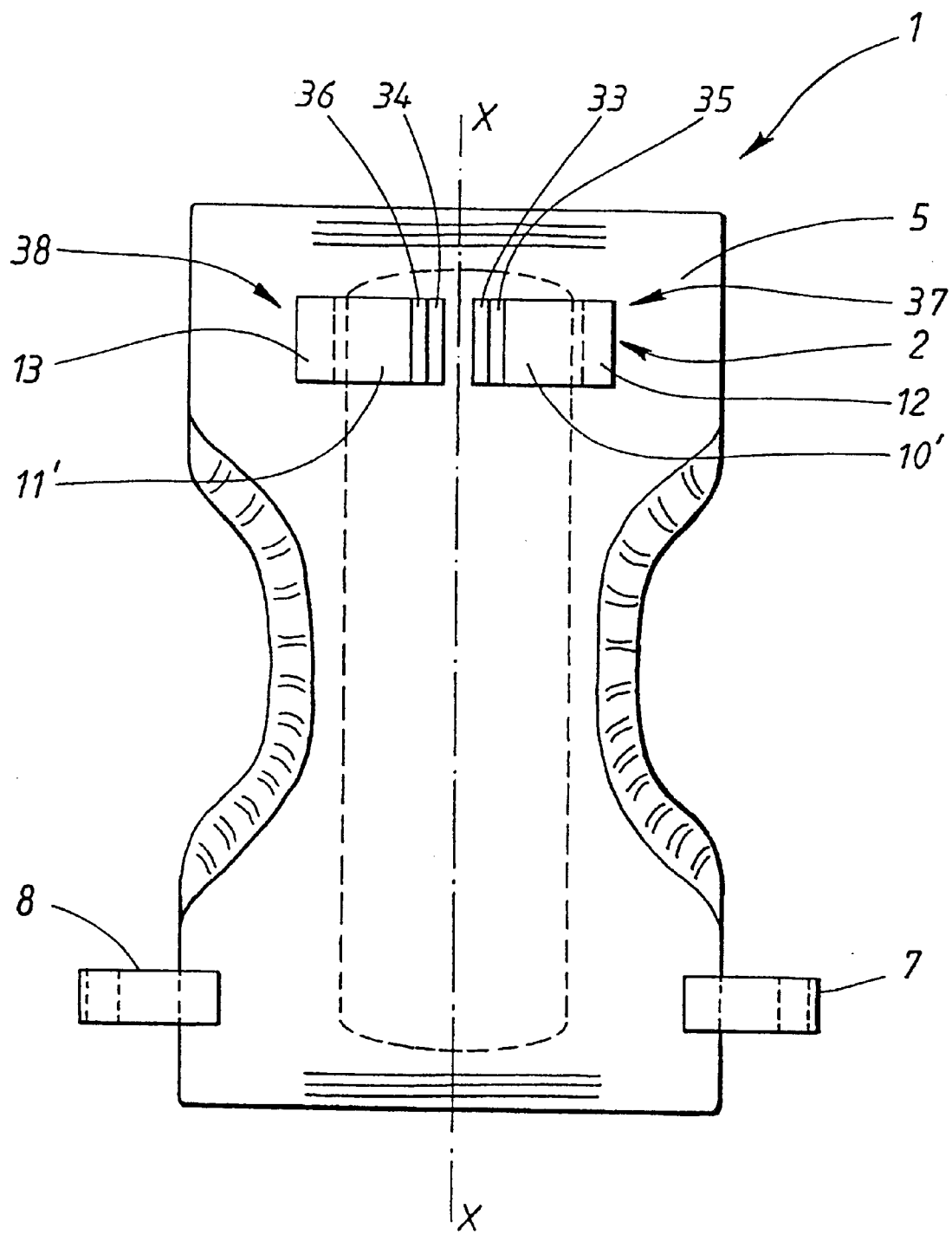
FIG. 6 shows one embodiment of a further aspect of the invention.

In another aspect of the inventive idea shown in FIG. 6, which comprises basically the same elements referred to previously, the attachment means 2 is divided into two strip sections 37 and 38 on either side of the longitudinal axis X—X. The figure is substantially the same as FIG. 1 and like elements are denoted with the same reference numerals. Where no reference numeral is indicated and no explanation is contained below it can be assumed that similar parts, and relationships of the various parts, are implied.

Each of said strip sections 37 and 38, which are of substantially identical construction, consists of four principal sections 12, 10', 33 and 35; 13, 11', 34 and 36 respectively. The innermost sections 33 and 34 designate parts of the strip sections which are attached to the backsheet 5. Similarly sections 12 and 13 are attached to the backsheet as in the previously described embodiments. The attachment of parts 33, 34, 12 and 13 is a fixed permanent attachment (e.g. by adhesive as explained above in connection with the previous embodiments) and which is able to withstand normal tension forces occurring during application of strips 7 and 8 when fitting the garment and during normal user movement.

Sections 35 and 36 constitute elastic sections similar to section 9 above. Each of said strips can thus be seen to be approximately equivalent to the strip element shown in FIG. 2, however being attached at their inner ends to the back sheet 5. Thus, taking strip 37, this would be similar to the basic strip structure shown in FIG. 2 for example, with the exception that section 11 in FIG. 2 would be much narrower and corresponds to section 33. However, at variance from corresponding surface 11 in FIG. 2, the outer surface of section 33 would preferably not be suitable for the attachment of tab strip 7. In this way only area 10' and zone 12 need be suitable for attachment of strip 7. Zones 35 and 36 are zones which preferably allow no cooperating attachment to strip 7.

A similar construction of the elastic section and non-elastic sections of said strip is thus foreseen for this embodiment as for the previously described embodiment of FIGS. 1 to 5. Consequently, zones 10' and 11' are equivalent to zones 10 and 11 in the previous embodiment and thus represent zones of non-attachment to the backsheet 5, whilst on their outer surface (i.e. facing away from the wearer), they have one part of the cooperating attachment means such as loop material for example.

The distance of separation of the innermost edges of strips may vary but is preferably small (e.g. 5 to 20 mm) so as to allow a large area for placement of the tabs 7 and 8 onto the areas 10' and 11'.

As will be clear from the aforegoing description, application of tabs 7 and 8 under tension to each of strips 37 and 38 will cause the elastic sections 35 and 36 to elastically extend, thus providing a good fit.

Contrary to the previously described embodiments, this aspect of the invention as shown in FIG. 6 however requires that the area of material of the backsheet between the attachment zones 33 and 34 is also able to withstand the tension forces applied to it during fitting and wearing the article as a result of the tab (7, 8) attachment. If necessary, dependent on the material of the back sheet, said zone could be strengthened by a strip of further material added thereto (either on the inside or outside of back sheet 5). Where further necessary such a strip may extend into, or through, the zones of attachment 33 and 34. Such a strip could be smaller or larger in all directions compared to the rectangular area between the inner edges of areas 34 and 33. This aspect of the invention may be used to achieve a materials saving whilst maintaining advantages of the previously described embodiments. Further advantages and features will be implicit to the skilled man upon reading this aspect of the invention.

What is claimed is:

1. An absorbent garment for use in absorbing bodily fluids, said garment having a first longitudinal side edge, a second longitudinal side edge, a front waist portion and a rear waist portion, said front waist portion being provided with front attachment means and said rear waist portion being provided with rear attachment means, said front and said rear attachment means providing cooperating surfaces allowing attachment of said front and rear attachment means together, wherein said garment has a longitudinal axis extending substantially between mid-portions of the front and rear waist portions, and wherein said front attachment means extends transversely with respect to said longitudinal axis, wherein said front attachment means comprises an attachment strip, said attachment strip comprising separate attachment portions and at least one elastic section comprising elastic material, wherein said attachment portions are each formed as a strip together with said at least one elastic section such that movement of said attachment portions away from each other causes stretching of said at least one elastic section, wherein said attachment portions are located between said first and second longitudinal side edges.

2. The absorbent garment according to claim 1, wherein said attachment strip extends transversely across said longitudinal axis.

3. The absorbent garment according to claim 1, wherein said front attachment means comprises two attachment strips extending transversely across said longitudinal axis.

4. The absorbent garment according to claim 1, wherein each of said attachment portions is a strip of attachment material, each of which is fixedly attached to an underlying strip of elastic material.

5. The absorbent garment according to claim 1, wherein said attachment strip has two end portions located on opposite sides of said longitudinal axis, and in that said attachment strip is attached to the front waist portion of the absorbent garment at said two end portions.

6. The absorbent garment according to claim 5, wherein said elastic section is further attached to said front waist portion at a location generally mid-way between said two end portions, and in that areas between said end portions and said location are zones of nonattachment with respect to said absorbent garment.

7. The absorbent garment according to claim 1, wherein said elastic material is in the form of a strip extending along the entire length of said attachment strip, and in that said attachment portions each extend along substantially half the length of said elastic material.

8. The absorbent garment according to claim 5, wherein said absorbent garment comprises an absorbent core lying with its own longitudinal axis substantially aligned with the longitudinal axis of said garment and having two longitudinal edges, and in that said end portions are attached to said waist portion outside said longitudinal edges.

9. The absorbent garment according to claim 6, wherein the attachment of said elastic section at said location midway between said two end portions is by means of an elastomeric adhesive.

10. The absorbent garment according to claim 1, wherein said front and said rear attachment means comprise cooperating releasable fastening means, and in that only one of said front and said rear attachment means has at least one elastic material section.

11. The absorbent garment according to claim 1, wherein said absorbent garment comprises an absorbent core having longitudinally opposed end edges, and in that said front attachment means has two opposed transverse edges, each of which edges is at a position located between said end edges of the absorbent core as seen in a direction along the longitudinal axis.

12. The absorbent garment according to claim 6, wherein attachment of said elastic section at said location midway between said two end portions has a width in a direction transverse to said longitudinal axis lying between 0.5 mm and 2 mm.

* * * * *